(12) United States Patent
Hecker

(10) Patent No.: US 7,339,183 B1
(45) Date of Patent: Mar. 4, 2008

(54) X-RAY CONVERSION METHOD

(76) Inventor: Joseph Hecker, 6030 Una-Del Dr., Rapid City, SD (US) 57702

( * ) Notice: Subject to any disclaimer, the term of this patent is extended or adjusted under 35 U.S.C. 154(b) by 0 days.

(21) Appl. No.: 11/701,067

(22) Filed: Jan. 31, 2007

(51) Int. Cl.
*A61B 6/00* (2006.01)

(52) U.S. Cl. ........................................ 250/583; 250/588

(58) Field of Classification Search ................ 250/580, 250/581, 582, 583, 584, 585, 586, 587, 588
See application file for complete search history.

(56) References Cited

U.S. PATENT DOCUMENTS 6,301,019 B1 * 10/2001 Saito et al. .................. 358/461
6,489,601 B1 * 12/2002 Huang ...................... 250/208.1
2007/0125973 A1 * 6/2007 Koishikawa ................ 250/588

* cited by examiner

*Primary Examiner*—David Porta
*Assistant Examiner*—Jessica L Eley
(74) *Attorney, Agent, or Firm*—Gene R. Woodle

(57) ABSTRACT

Embodiments of an x-ray converter are disclosed in which a conventional PSP and computed digital radiology equipment may be used with the converter to convert an analog x-ray image into a digital image.

4 Claims, 1 Drawing Sheet

X-RAY CONVERSION METHOD

BACKGROUND OF THE INVENTION

1. Field of the Invention

The present invention relates generally to the area of X-rays and more particularly to the conversion of X-ray film images to digital X-ray images.

2. Background Information

X-rays are among the most reliable and useful diagnostic tools in the treatment of injury and disease in both humans and animals. Although there are a variety of x-ray image systems, the most often used may be classified as either traditional x-ray film images or digital radiology.

In a traditional x-ray film system, an image is captured on a chemically treated x-ray film. The film is sensitive to radiation (usually x-rays) and exposure to x-rays causes the film to turn dark. X-rays tend to pass through materials such as muscle and skin, but are largely blocked by material such as bone. When a hand, for example, is interposed between x-ray film and the x-ray source, more of the x-rays are blocked by the bone in the hand than by the soft tissue in the hand and areas shadowed by the bone don't turn as dark. This results in a typical x-ray image with the more dense areas (bone) appearing white and the less dense areas being darker or black. Traditional x-ray film images are often referred to as being analog images.

Digital radiology (DR) produces an image similar to a traditional x-ray, but does not rely upon a reaction in a chemically treated film to an x-ray. DR uses an electronic plate to create a digital image which is ordinarily produced and stored in a computer. DR images aren't technically film x-rays, but they have the same general diagnostic use and appearance.

Traditional film x-ray systems and DR imaging systems have advantages and disadvantages. One of the chief advantages of traditional x-ray systems is a much lower initial cost. One of the chief advantages of a DR imaging system is the ability to manipulate the DR image after it is captured and saved on a computer. Various software is available for manipulating a DICOM image. DICOM is a widely accepted format for medical imaging. Unlike a traditional x-ray image, a DR image may be changed and enhanced by various operations such as cropping, edge enhancement, enlarging, changing contrast, and changing brightness.

Computed radiology (CR) is a kind of hybrid of traditional x-ray technology and DR image technology. CR systems use the same method of capturing an image as a traditional film x-ray system except instead of capturing the image on x-ray film, the image is captured on a photostimulable phosphor plate (PSP). The exposed PSP is scanned by a plate reader and the image is captured in DICOM format and may be manipulated using software in the same manner as a DR image. The traditional analog x-ray film image may be converted into a digital image by using a CR imaging system.

It is often necessary or desirable to change a traditional analog x-ray film image into a digital image which may be manipulated in the same manner as a DR image. For example, a doctor may want to compare an old x-ray captured on traditional x-ray film with a more recent image captured using DR or CR technology. Currently an analog X-ray film image may be converted to a digital image by taking a digital camera photograph of the old x-ray under very specific and controlled conditions. Most often these images are in a JPEG format and may be saved and manipulated to a very limited extent using conventional photo modification software. A JPEG image is not a useful as a DICOM format image because DICOM image software can be used to perform significant enhancements of the image which are not available when manipulating a JPEG image. For example, using conventional software, a DICOM image may be manipulated such that soft tissue such as a lung is emphasized and the bone portion of the image reduced.

The x-ray conversion method of the instant invention solves several problems relating to the conversion of traditional film analog x-ray images to digital images which may be manipulated and enhanced in the same manner as images created directly using a digital imaging system. The instant invention provides a method for directly converting traditional x-ray images to DICOM images using an inexpensive device coupled with existing CR equipment. In some instances, it may actually be possible to correct errors in the original X-ray film image.

The ideal x-ray conversion method should provide a simple method of converting traditional x-ray images to DICOM images with little or no loss of detail or accuracy. The ideal x-ray conversion method should take advantage of existing CR imaging equipment and software where possible. The ideal x-ray conversion method should also be rugged, inexpensive, easy to service, and easy to operate.

SUMMARY OF THE INVENTION

The x-ray conversion method of the instant invention is a method of converting traditional x-ray film images to digital DICOM images using a converter coupled with existing computed radiology (CR) equipment. The instant invention also involves the use of a conventional photostimulable phosphor plate (PSP) in a new and unique way.

The converter is a box with a drawer which slides into and out of the box. A conventional PSP is placed in the drawer and slid into the box. The PSP is exposed to ultraviolet light inside the box for sufficient time to totally blacken the PSP. (Although ultraviolet light is used, shorter wavelengths such as X-rays would also work.) The x-ray film image to be duplicated is placed on top of the blackened PSP. The PSP is then exposed to ordinary white light inside the box. The white light passes through the lighter portions of the x-ray image and is blocked by the darker portions. (Although white light is used, higher wavelengths such as infrared would also work) The lighter the area of the x-ray image the more light is allowed to pass through. This has the effect of creating an exact gray scale reproduction of the x-ray image on the PSP.

The PSP may then be processed using conventional CR technology in the usual manner. That is, the PSP is scanned using a CR scanner or reader and a DICOM format image produced which may be enhanced, manipulated, stored, transmitted, or printed in the same manner as any other DICOM image using the CR system software.

One of the major objects of the present invention is to provide a simple method of converting traditional x-ray film images to DICOM images with little or no loss of detail or accuracy.

Another objective of the present invention is the x-ray conversion method which takes advantage of existing CR equipment and software where possible.

Another objective of the present invention is to provide a method and device which is rugged, inexpensive, easy to service, and easy to operate.

These and other features of the invention will become apparent when taken in consideration with the following detailed description and the drawings.

DESCRIPTION OF A PREFERRED EMBODIMENT

Figure 1:
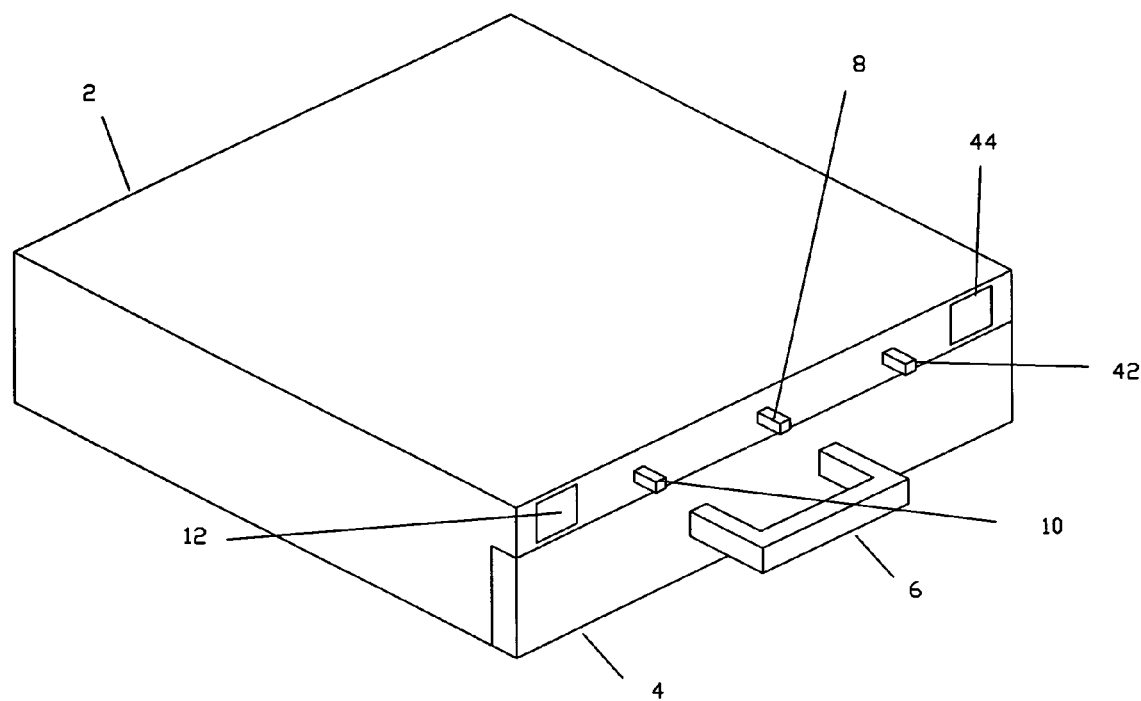
FIG. 1 is an orthographic view of the converter of the instant invention.
Figure 2:
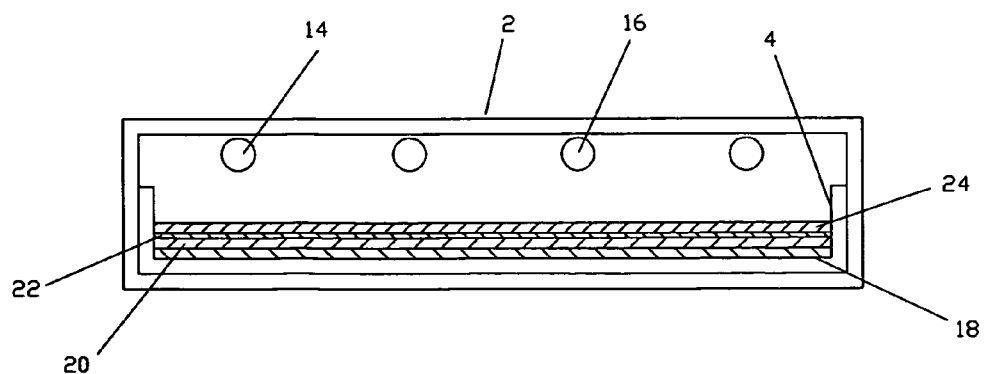
FIG. 2 is a sectional view taken along line 2-2 of FIG. 1.

Referring to the drawing, FIGS. 1 and 2, a preferred embodiment of the x-ray conversion method of the instant invention is shown.

Referring now to FIG. 1, the converter of the instant invention includes a box 2 with a drawer 4 which slides into and out of the box 2. The drawer 4 includes a handle 6. The box 2 further includes an on/off switch 8, a conditioning switch 10, a conditioning timer 12, a duplication switch 42, and a duplication timer 44.

Referring now to FIG. 2, a sectional view of the converter of the instant invention taken along line 2-2 of FIG. 1 is shown. This view shows how said drawer 4 fits within said box 2. An ultraviolet light source 14 is affixed inside said box 2 near the top of said box 2. (Although ultraviolet light is used, shorter wavelengths such as X-rays would also work.) A white light source 16 is also affixed inside said box 2 near the top of said box 2. (Although white light is used, higher wavelengths such as infrared would also work) A pad 18 is affixed to the top of the inside surface of said drawer 4. The pad 18 may be any type of foam surface to provide a cushion. A conventional PSP 20 may be laid on top of said pad 18. A piece of conventional x-ray film 22 may be laid on top of the PSP 20. A glass plate 24 may be laid on top of the x-ray film 22 or on top of said PSP 20.

The converter of the instant invention is wired conventionally such that electric power may be provided to the ultraviolet light source 14, the white light source 16, the conditioning timer 12, and the duplication timer 44. Power is supplied to all circuits through said on/off switch 8 and though said on/off switch 8 to said ultraviolet light source 14, said white light source 16, said conditioning timer 12, said duplication timer 44, said conditioning switch 10 and said duplication switch 42. Said on/off switch 8 may be used to turn the power on or off. Said conditioning switch 10 directs power to said ultraviolet light source 14 and said conditioning timer 12 is interposed between said on/off switch 8 and said conditioning switch 10 such that the amount of time said ultraviolet light source 14 is on is controlled by said conditioning timer 12. Said duplication switch 42 directs power to said white light source 16 and said duplication timer 44 is interposed between said on/off switch 8 and said duplication switch 42 such that the amount of time said white light source 16 is on is controlled by said duplication timer 44. Said on/off switch 8, said conditioning switch 10, said conditioning timer 12, said ultraviolet light source 14, said duplication switch 42, and said white light source 16 are all conventional and easily available.

In operation, said PSP 20 is laid on said pad 18 and the glass plate 24 is laid on top of said PSP 20. Said drawer 4 is slid into said box 2. Said conditioning switch 10 is set to direct power to said ultraviolet light source 14 and said conditioning timer 12 is set to the appropriate exposure time to ensure that said PSP 20 will be totally blackened when exposed to ultraviolet light. Said on/off switch 8 is then turned on and said PSP 20 exposed. In the preferred embodiment, said ultraviolet light source 14 is switched on for 50 seconds, but other exposure times could be used provided that said PSP 20 is totally blackened. Said drawer 4 is slid from said box 2, said x-ray film 22 laid on top of said PSP 20 and said glass plate 24 laid on said x-ray film 22. Said drawer 4 is slid back inside said box 2. Said duplication switch 42 is set to direct power to said white light source 16 and said duplication timer 42 is set to the appropriate time to create an accurate image on said PSP 20 when white light is directed through said x-ray film 22 onto said PSP 20. Of course, said conditioning switch 10 is off for this operation. Said on/off switch 8 is turned on and said PSP 20 exposed to light from said white light source 16. In the preferred embodiment, said white light source 16 is turned on for 20 seconds, but other times could be used provided that the time is correct to create and accurate image on said PSP 20. Said PSP may then be scanned and processed in the usual manner using a conventional CR scanner and software to produce a DICOM image which may be enhanced, manipulated, stored, transmitted, or printed in the same manner as any other DICOM image using the CR software.

In the preferred embodiment said white light source 16 consists of 2 eighty watt bulbs and said ultraviolet light source 14 consists of 3 one hundred twenty watt bulbs all of which are conventional. Of course, other light sources which accomplish the same affects could be used. In the preferred embodiment said case 2 is plastic, but could be made from wood or other materials having similar characteristics. All other elements are conventional.

While preferred embodiments of this invention have been shown and described above, it will be apparent to those skilled in the art that various modifications may be made in these embodiments without departing from the spirit of the present invention.

I claim:

1. A method for converting a traditional film x-ray image into a digital image using a conventional photostimulable phosphor plate or PSP comprising:
    (1) exposing a PSP to one of ultraviolet light and a light having a shorter wavelength than ultraviolet light for sufficient time to totally blacken the PSP;
    (2) placing an x-ray film image over the totally blackened PSP; and
    (3) exposing the totally blackened PSP to one of white light and a light having a wavelength higher than white light, with the x-ray film image being between the white light and the totally blackened PSP, for sufficient time to create a gray scale reproduction of said x-ray film image on said PSP;
    whereby, a conventional film x-ray image may be transferred to a PSP.

2. The method of claim 1 in which the exposing a PSP is to light having a shorter wavelength than ultraviolet light.

3. The method of claim 1 in which the exposing the totally blackened PSP is to light having a wavelength higher than white light.

4. A method for converting a traditional film x-ray image to a digital image using a conventional photostimulable phosphor plate or PSP comprising:
    (1) exposing a PSP to light having a shorter wavelength than ultraviolet light for sufficient time to totally blacken the PSP;

(2) placing an x-ray film image over the totally blackened PSP; and
(3) exposing the totally blackened PSP to light having a wavelength higher than white light, with the x-ray film image being between the light having a wavelength higher than white light and the totally blackened PSP, for sufficient time to create a gray scale reproduction of said x-ray film image on said PSP;

whereby, a conventional film x-ray image may be transferred to a PSP.

* * * * *